US008795326B2

(12) United States Patent
Richard

(10) Patent No.: US 8,795,326 B2
(45) Date of Patent: Aug. 5, 2014

(54) EXPANDING SEAL ANCHOR FOR SINGLE INCISION SURGERY

(75) Inventor: Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 1049 days.

(21) Appl. No.: 12/244,127

(22) Filed: Oct. 2, 2008

(65) Prior Publication Data

US 2009/0093850 A1 Apr. 9, 2009

Related U.S. Application Data

(60) Provisional application No. 60/997,844, filed on Oct. 5, 2007.

(51) Int. Cl.
*A61B 1/32* (2006.01)

(52) U.S. Cl.
USPC .......................................... 606/206; 600/206

(58) Field of Classification Search
USPC ........ 606/213; 604/105–108, 164.01, 164.03, 604/164.06, 164.08, 164.09, 164.1, 164.11, 604/164.12, 174, 176, 256, 268; 600/206, 600/208, 210
See application file for complete search history.

(56) References Cited

U.S. PATENT DOCUMENTS

| | | | |
|---|---|---|---|
| 219,296 | A | 9/1879 | Naylor, Jr. |
| 319,296 | A | 6/1885 | Molesworth |
| 668,879 | A | 2/1901 | Miller |
| 702,789 | A | 6/1902 | Gibson |
| 1,213,001 | A | 1/1917 | Phillips |
| 1,248,492 | A | 12/1917 | Hill |
| 2,548,602 | A | 4/1948 | Greenburg |
| 2,566,499 | A | 9/1951 | Richter |
| 3,308,819 | A | 3/1967 | Arp |
| 67,545 | A | 8/1967 | Hodgins et al. |
| 3,509,883 | A | 5/1970 | Dibelius |
| 3,545,443 | A | 12/1970 | Ansari |
| 3,653,388 | A | 4/1972 | Tenckhoff |
| 3,742,958 | A | 7/1973 | Rundles |
| 3,750,667 | A | 8/1973 | Pshenichny et al. |

(Continued)

FOREIGN PATENT DOCUMENTS

| | | |
|---|---|---|
| DE | 3321621 A1 | 12/1984 |
| DE | 3713831 A1 | 12/1988 |

(Continued)

OTHER PUBLICATIONS

European Search Report for corresponding EP 08253232 date of mailing is Feb. 11, 2009 (3 pages).

(Continued)

*Primary Examiner* — Christian Sevilla

(57) ABSTRACT

The present disclosure relates to a surgical anchoring apparatus for use during a minimally invasive surgical procedure. The surgical anchoring apparatus includes a body member and a dilator element at least partially positionable therein. The body member includes a grip segment adapted for manual engagement by a user and an expandable section having a plurality of expandable segments and a plurality of cam surfaces. The grip segment resiliently transitions between a first or normal state and a second state in which the grip segment is at least partially inverted. The expandable section's cam surfaces are configured to engage a distal end of the dilator element upon its insertion such that the expandable section may transition from an initial condition to an expanded condition in which the body member is secured or anchored within an incision in tissue.

29 Claims, 4 Drawing Sheets

(56) References Cited

U.S. PATENT DOCUMENTS 3,788,318 A 1/1974 Kim et al.
3,789,852 A 2/1974 Kim et al.
3,811,449 A 5/1974 Gravlee et al.
3,856,021 A 12/1974 McIntosh
3,877,427 A 4/1975 Alexeev
3,893,454 A 7/1975 Hagelin
3,902,492 A 9/1975 Greenhalgh
3,952,742 A 4/1976 Taylor
3,968,800 A 7/1976 Vilasi
4,018,230 A 4/1977 Ochiai et al.
4,141,364 A 2/1979 Schultze
4,183,102 A 1/1980 Guiset
4,204,541 A 5/1980 Kapitanov
4,320,762 A 3/1982 Bentov
4,402,685 A 9/1983 Bühler et al.
4,411,655 A 10/1983 Schreck
4,447,237 A 5/1984 Frisch et al.
4,461,281 A 7/1984 Carson
4,479,497 A 10/1984 Fogarty et al.
4,493,701 A 1/1985 Bootman et al.
RE31,855 E 3/1985 Osbourne
4,504,268 A 3/1985 Herlitze
4,578,061 A 3/1986 Lemelson
4,581,019 A 4/1986 Curelaru et al.
4,581,025 A 4/1986 Timmermans
4,585,437 A 4/1986 Simms
4,589,868 A 5/1986 Dretler
4,601,713 A 7/1986 Fuqua
4,610,668 A 9/1986 Fleig
4,630,609 A 12/1986 Chin
4,650,466 A 3/1987 Luther
4,706,670 A 11/1987 Andersen et al.
4,716,901 A 1/1988 Jackson et al.
4,738,666 A 4/1988 Fuqua
4,739,762 A 4/1988 Palmaz
4,753,636 A 6/1988 Free
4,772,266 A 9/1988 Groshong
4,798,193 A 1/1989 Giesy et al.
4,817,587 A 4/1989 Janese
4,846,791 A 7/1989 Hattler et al.
4,846,812 A 7/1989 Walker et al.
4,865,593 A 9/1989 Ogawa et al.
4,869,717 A 9/1989 Adair
4,888,000 A 12/1989 McQuilkin et al.
4,896,669 A 1/1990 Bhate et al.
4,899,729 A 2/1990 Gill et al.
4,921,479 A 5/1990 Grayzel
4,941,874 A 7/1990 Sandow et al.
4,954,126 A 9/1990 Wallsten
4,955,895 A 9/1990 Sugiyama et al.
4,972,827 A 11/1990 Kishi et al.
4,986,830 A 1/1991 Owens et al.
4,996,583 A 2/1991 Hatada
4,998,539 A 3/1991 Delsanti
5,002,557 A 3/1991 Hasson
5,002,577 A 3/1991 Bolesky et al.
5,009,643 A 4/1991 Reich et al.
5,021,241 A 6/1991 Yamahira et al.
D318,733 S 7/1991 Wyzgala
5,041,093 A 8/1991 Chu
5,045,056 A 9/1991 Behl
5,069,674 A 12/1991 Fearnot et al.
5,100,388 A 3/1992 Behl et al.
5,104,388 A 4/1992 Quackenbush
5,112,304 A 5/1992 Barlow et al.
5,116,318 A 5/1992 Hillstead
5,122,122 A 6/1992 Allgood
5,139,485 A 8/1992 Smith et al.
5,139,511 A 8/1992 Gill et al.
5,141,497 A 8/1992 Erskine
5,147,316 A 9/1992 Castillenti
5,158,545 A 10/1992 Trudell et al.
5,176,128 A 1/1993 Andrese
5,183,464 A 2/1993 Dubrul et al.
5,183,465 A 2/1993 Xanthakos et al.
5,188,602 A 2/1993 Nichols
5,197,971 A 3/1993 Bonutti
5,201,756 A 4/1993 Horzewski et al.
5,207,647 A 5/1993 Phelps
5,221,263 A 6/1993 Sinko et al.
5,222,938 A 6/1993 Behl
5,222,971 A 6/1993 Willard et al.
5,226,899 A 7/1993 Lee et al.
5,230,702 A 7/1993 Lindsay et al.
5,234,425 A 8/1993 Fogarty et al.
5,246,424 A 9/1993 Wilk
5,248,298 A 9/1993 Bedi et al.
5,250,025 A 10/1993 Sosnowski et al.
5,250,033 A 10/1993 Evans et al.
5,261,888 A 11/1993 Semm
5,275,611 A 1/1994 Behl
5,279,554 A 1/1994 Turley
5,279,567 A 1/1994 Ciaglia et al.
5,312,360 A 5/1994 Behl
5,312,417 A 5/1994 Wilk
5,316,360 A 5/1994 Fetkma
5,318,542 A 6/1994 Hirsch et al.
5,318,588 A 6/1994 Horzewski et al.
5,320,611 A 6/1994 Bonutti et al.
5,330,501 A 7/1994 Tovey et al.
5,353,785 A 10/1994 Wilk
D352,018 S 11/1994 Robert et al.
5,380,290 A 1/1995 Makower et al.
5,392,766 A 2/1995 Masterson et al.
5,403,278 A 4/1995 Ernst et al.
5,405,334 A 4/1995 Roth et al.
5,407,427 A 4/1995 Zhu et al.
5,407,430 A 4/1995 Peters
5,409,469 A 4/1995 Schaerf
D358,465 S 5/1995 Klein et al.
5,415,178 A 5/1995 Hsi et al.
5,431,676 A 7/1995 Dubrul et al.
5,433,708 A 7/1995 Nichols et al.
5,437,631 A 8/1995 Janzen
5,443,484 A 8/1995 Kirsch et al.
5,453,094 A 9/1995 Metcalf et al.
5,454,790 A 10/1995 Dubrul
5,458,579 A 10/1995 Chodorow et al.
5,460,170 A 10/1995 Hammerslag
5,460,607 A 10/1995 Miyata et al.
5,484,403 A 1/1996 Yoakum et al.
5,487,739 A 1/1996 Aebischer et al.
5,489,279 A 2/1996 Meserol
5,496,292 A 3/1996 Burnham
5,527,276 A 6/1996 Bruce
5,533,986 A 7/1996 Mottola et al.
5,540,658 A 7/1996 Evans et al.
5,542,928 A 8/1996 Evans et al.
5,556,376 A 9/1996 Yoon et al.
5,569,200 A 10/1996 Umeno et al.
5,573,511 A * 11/1996 Yoon ........................ 604/164.12
5,573,517 A 11/1996 Bonutti et al.
5,577,993 A 11/1996 Zhu et al.
5,647,859 A 7/1997 Lampropoulos et al.
5,647,860 A 7/1997 Roth et al.
5,665,076 A 9/1997 Roth et al.
5,672,168 A 9/1997 de la Torre et al.
5,674,240 A 10/1997 Bonutti et al.
5,683,347 A 11/1997 Miyata et al.
5,695,462 A 12/1997 Sutcu et al.
5,713,867 A 2/1998 Morris
5,743,882 A 4/1998 Luther
5,772,639 A 6/1998 Lampropoulos et al.
5,797,886 A 8/1998 Roth et al.
5,800,390 A 9/1998 Hayakawa et al.
5,800,409 A 9/1998 Bruce
5,814,058 A 9/1998 Carlson et al.
5,817,062 A * 10/1998 Flom et al. .................... 604/174
5,817,072 A 10/1998 Lampropoulos et al.
5,827,319 A 10/1998 Carlson et al.
5,836,913 A 11/1998 Orth et al.
5,885,217 A 3/1999 Gisselberg et al.
5,938,587 A 8/1999 Taylor et al.
5,938,645 A 8/1999 Gordon

(56) References Cited

U.S. PATENT DOCUMENTS

| | | | | |
|---|---|---|---|---|
| 5,957,913 | A | 9/1999 | de la Torre et al. | |
| 5,961,499 | A | 10/1999 | Bonutti et al. | |
| 6,004,341 | A | 12/1999 | Zhu et al. | |
| 6,024,736 | A | 2/2000 | de la Torre et al. | |
| 6,027,480 | A | 2/2000 | Davis et al. | |
| 6,030,364 | A | 2/2000 | Durgin et al. | |
| 6,030,402 | A | 2/2000 | Thompson et al. | |
| 6,056,766 | A | 5/2000 | Thompson et al. | |
| 6,077,250 | A | 6/2000 | Snow et al. | |
| 6,080,174 | A | 6/2000 | Dubrul et al. | |
| 6,090,072 | A | 7/2000 | Kratoska et al. | |
| 6,095,967 | A | 8/2000 | Black et al. | |
| 6,139,532 | A | 10/2000 | Howell et al. | |
| 6,245,052 | B1 | 6/2001 | Orth et al. | |
| 6,273,874 | B1 | 8/2001 | Parris | |
| 6,273,899 | B1 | 8/2001 | Kramer | |
| 6,287,322 | B1 | 9/2001 | Zhu et al. | |
| 6,315,770 | B1 | 11/2001 | de la Torre et al. | |
| 6,319,246 | B1 | 11/2001 | de la Torre et al. | |
| 6,325,789 | B1 | 12/2001 | Janzen et al. | |
| 6,325,812 | B1 | 12/2001 | Dubrul et al. | |
| 6,338,730 | B1 | 1/2002 | Bonutti et al. | |
| 6,363,273 | B1 | 3/2002 | Mastrorio et al. | |
| 6,368,337 | B1 | 4/2002 | Kieturakis et al. | |
| 6,398,799 | B2 | 6/2002 | Kramer | |
| 6,402,722 | B1 | 6/2002 | Snow et al. | |
| 6,420,550 | B2 | 7/2002 | Elsas, II et al. | |
| 6,425,908 | B2 | 7/2002 | Ravenscroft et al. | |
| 6,428,511 | B2 | 8/2002 | Manhes | |
| 6,447,527 | B1 | 9/2002 | Thompson et al. | |
| 6,447,540 | B1 | 9/2002 | Fontaine et al. | |
| 6,450,989 | B2 | 9/2002 | Dubrul et al. | |
| 6,463,361 | B1 | 10/2002 | Wang et al. | |
| 6,464,690 | B1 | 10/2002 | Castañneda et al. | |
| 6,482,175 | B1 | 11/2002 | Walker | |
| 6,494,893 | B2 | 12/2002 | Dubrul et al. | |
| 6,500,170 | B2 | 12/2002 | Palmer et al. | |
| 6,503,245 | B2 | 1/2003 | Palmer et al. | |
| 6,524,326 | B1 | 2/2003 | Zhu et al. | |
| 6,564,078 | B1 | 5/2003 | Marino et al. | |
| 6,572,624 | B2 * | 6/2003 | U et al. | 606/130 |
| 6,572,631 | B1 | 6/2003 | McCartney | |
| 6,579,281 | B2 | 6/2003 | Palmer et al. | |
| 6,592,573 | B2 | 7/2003 | Castañeda et al. | |
| D480,140 | S | 9/2003 | Harding et al. | |
| 6,679,900 | B2 | 1/2004 | Kieturakis et al. | |
| 6,685,721 | B1 | 2/2004 | Kramer | |
| 6,692,465 | B2 | 2/2004 | Kramer | |
| 6,695,856 | B2 | 2/2004 | Kieturakis et al. | |
| 6,712,795 | B1 | 3/2004 | Cohen | |
| 6,714,841 | B1 | 3/2004 | Wright et al. | |
| 6,726,699 | B1 | 4/2004 | Wright et al. | |
| 6,728,599 | B2 | 4/2004 | Wang et al. | |
| 6,758,853 | B2 | 7/2004 | Kieturakis et al. | |
| 6,785,593 | B2 | 8/2004 | Wang et al. | |
| 6,793,653 | B2 | 9/2004 | Sanchez et al. | |
| 6,799,088 | B2 | 9/2004 | Wang et al. | |
| 6,821,287 | B1 | 11/2004 | Jang | |
| 6,824,554 | B1 | 11/2004 | Jang | |
| 6,836,703 | B2 | 12/2004 | Wang et al. | |
| 6,839,612 | B2 | 1/2005 | Sanchez et al. | |
| 6,840,951 | B2 | 1/2005 | de la Torre et al. | |
| 6,852,107 | B2 | 2/2005 | Wang et al. | |
| 6,871,117 | B2 | 3/2005 | Wang et al. | |
| 6,887,194 | B2 | 5/2005 | Hart et al. | |
| 6,890,342 | B2 | 5/2005 | Zhu et al. | |
| 6,892,112 | B2 | 5/2005 | Wang et al. | |
| 6,951,535 | B2 | 10/2005 | Ghodoussi et al. | |
| 6,953,467 | B2 | 10/2005 | Kieturakis et al. | |
| 6,964,675 | B2 | 11/2005 | Zhu et al. | |
| 6,965,812 | B2 | 11/2005 | Wang et al. | |
| 7,008,377 | B2 | 3/2006 | Beane et al. | |
| 7,070,586 | B2 | 7/2006 | Hart et al. | |
| 7,074,231 | B2 | 7/2006 | Jang | |
| 7,094,218 | B2 | 8/2006 | Rome et al. | |
| 7,144,413 | B2 | 12/2006 | Wilford et al. | |
| 7,179,272 | B2 | 2/2007 | Kieturakis et al. | |
| 7,189,249 | B2 | 3/2007 | Hart et al. | |
| 7,214,236 | B2 | 5/2007 | Kieturakis et al. | |
| 7,217,240 | B2 | 5/2007 | Snow | |
| 7,229,460 | B2 | 6/2007 | Kramer | |
| 7,239,940 | B2 | 7/2007 | Wang et al. | |
| 7,294,136 | B2 | 11/2007 | Dubrul et al. | |
| 7,297,153 | B2 | 11/2007 | Kieturakis et al. | |
| 7,300,448 | B2 | 11/2007 | Criscuolo et al. | |
| 7,309,328 | B2 | 12/2007 | Kaplan et al. | |
| 7,408,439 | B2 | 8/2008 | Wang et al. | |
| 7,413,565 | B2 | 8/2008 | Wang et al. | |
| 7,422,571 | B2 | 9/2008 | Schweikert et al. | |
| 7,449,011 | B2 | 11/2008 | Wenchell et al. | |
| 7,608,082 | B2 | 10/2009 | Cuevas et al. | |
| 2002/0035373 | A1 | 3/2002 | Carlson et al. | |
| 2003/0100909 | A1 * | 5/2003 | Suzuki | 606/120 |
| 2006/0162672 | A1 * | 7/2006 | Dokken | 119/707 |
| 2008/0188897 | A1 * | 8/2008 | Krebs et al. | 606/300 |

FOREIGN PATENT DOCUMENTS

| | | | |
|---|---|---|---|
| DE | 4020956 | A1 | 6/1990 |
| DE | 91 02 553.2 | | 7/1991 |
| DE | 91 06 553.4 | | 9/1991 |
| EP | 0 177 177 | | 4/1986 |
| EP | 0 385 920 | A2 | 9/1990 |
| EP | 0 391 396 | | 10/1990 |
| EP | 0 487 175 | A1 | 5/1992 |
| EP | 1523948 | A | 4/2005 |
| EP | 1702575 | A | 9/2006 |
| FR | 748666 | | 7/1933 |
| FR | 2 439 591 | | 5/1980 |
| GB | 2 154 608 | | 9/1985 |
| GB | 2 199 247 | | 7/1988 |
| JP | 57-43726 | | 3/1982 |
| JP | 57-197901 | | 12/1982 |
| JP | 08-019550 | | 1/1996 |
| SU | 1331495 | A1 | 8/1987 |
| SU | 1528465 | A1 | 12/1989 |
| WO | WO 89/04638 | | 6/1989 |
| WO | WO 92/19312 | | 11/1992 |
| WO | WO 92/21294 | | 12/1992 |
| WO | WO 95/30374 | | 11/1995 |
| WO | WO 98/19730 | | 5/1998 |
| WO | WO 98/29026 | | 7/1998 |
| WO | WO 99/06094 | | 2/1999 |
| WO | WO99/17665 | A | 4/1999 |
| WO | WO 03/011154 | | 2/2003 |
| WO | WO2004/047654 | A | 6/2004 |
| WO | WO 2005/03233 | 1 | 4/2005 |

OTHER PUBLICATIONS

Japanese Office Action 2008-259099 dated Jan. 23, 2013.

* cited by examiner

EXPANDING SEAL ANCHOR FOR SINGLE INCISION SURGERY

CROSS REFERENCE TO RELATED APPLICATION

The present application claims the benefit of and priority to U.S. Provisional Application Ser. No. 60/997,844 filed on Oct. 5, 2007, the entire contents of which are incorporated herein by reference.

BACKGROUND

1. Technical Field

The present disclosure relates to a device, and a method of use thereof, for facilitating access to a patient's internal cavities during a surgical procedure. More particularly, the present disclosure relates to a surgical anchoring apparatus adapted for insertion into an incision in tissue, and for the sealed reception of one or more surgical objects, so as to form a substantially fluid-tight seal with both the tissue and the surgical object, or objects.

2. Background of the Related Art

Today, many surgical procedures are performed through small incisions in the skin, as compared to the larger incisions typically required in traditional procedures, in an effort to reduce trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures. During a typical minimally invasive procedure, surgical objects, such as surgical access devices, e.g. trocar and cannula assemblies, or endoscopes, are inserted into the patient's body through the incision in tissue.

In generally, prior to the introduction of the surgical object into the patient's body, insufflation gasses are used to enlarge the area surrounding the target surgical site to create a larger, more accessible work area. Accordingly, the maintenance of a substantially fluid-tight seal at the incision and about the surgical object, or objects, is desirable so as to prevent the escape of the insufflation gases and the deflation or collapse of the enlarged surgical work area.

To this end, various apparatus, including valves, seals and the like, are used during the course of minimally invasive procedures and are widely known in the art. However, a continuing need exists for a self-anchoring apparatus that can be inserted directly into the incision in tissue and that can accommodate a variety of surgical objects while maintaining the integrity of an insufflated workspace.

SUMMARY

In one aspect of the present disclosure, a surgical anchoring apparatus includes a body member defining a longitudinal body passage extending along a longitudinal axis thereof, a dilator element at least partially positionable within the longitudinal passage of the body member and a seal mounted with respect to the dilator element.

The body member includes an expandable section adapted to transition between a first initial condition and a second expanded condition. The expandable section of the body member includes a plurality of expandable segments separated by slots, which may be substantially longitudinal, and a plurality of internal cam surfaces that are obliquely arranged with respect to the longitudinal axis defined by the body member. In one embodiment, each of the expandable segments includes an internal cam surface. The expandable section further includes an outer helical thread adapted to facilitate the advancement of the body member within tissue when the body member is in the first initial condition.

The body member also includes a grip segment adapted for manual engagement by a user. The grip segment depends radially outwardly relative to the longitudinal axis of the body member. The grip segment is adapted to transition between a normal state and an at least partially inverted state. The grip segment may comprise an elastomeric material, and have a peripheral flange that is adapted to contact tissue when the grip segment is in the normal state. The peripheral flange may be adapted to establish a vacuum seal with the tissue upon transition of the grip segment from the at least partially inverted state to the normal state.

The dilator element is dimensioned to cause the expandable section to transition to the second expanded condition when inserted into the expandable section to thereby facilitate securement of the body member relative to tissue. The dilator element defines a longitudinal dilator passage for the reception and passage of a surgical object. The dilator element is dimensioned to contact the cam surfaces during insertion of the dilator element within the longitudinal passage of the body member to move the expandable segments at least radially outwardly relative to the longitudinal axis and cause the transition of the expandable section to the second expanded condition.

The seal is adapted to establish a substantial sealing relation with the surgical object received within the dilator element. In alternate embodiments, the seal may include a gel material or a self healing foam material.

These and other features of the valve disclosed herein will become more readily apparent to those skilled in the art from the following detailed description of various embodiments of the present disclosure.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
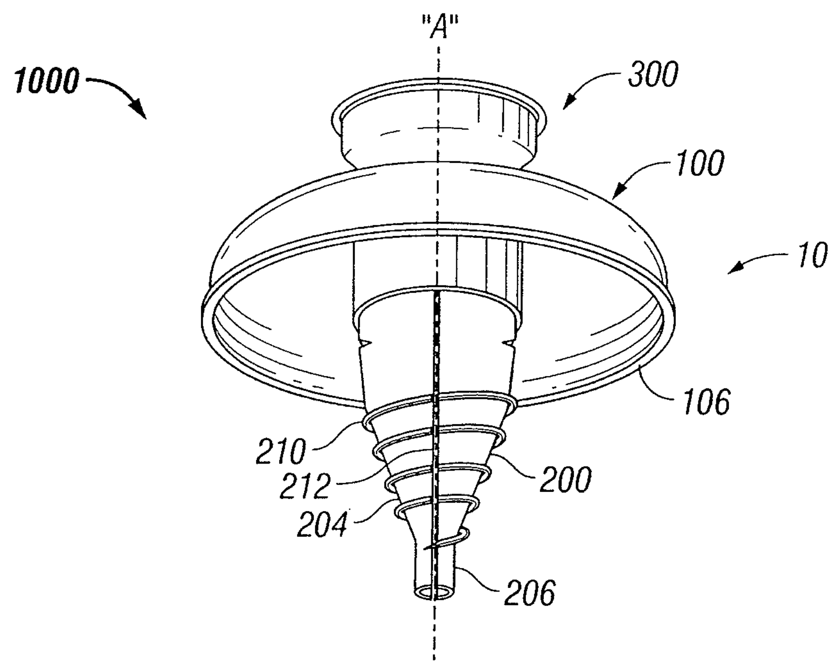
FIG. 1 is a side perspective view of a surgical anchoring apparatus in accordance with the principles of the present disclosure illustrating a body member and a dilator element.

In the drawings and in the description which follows, in which like reference numerals identify similar or identical elements, the term “proximal” will refer to the end of the apparatus which is closest to the clinician during the use thereof, while the term “distal” will refer to the end which is furthest from the clinician, as is traditional and known in the art.

Figure 2:
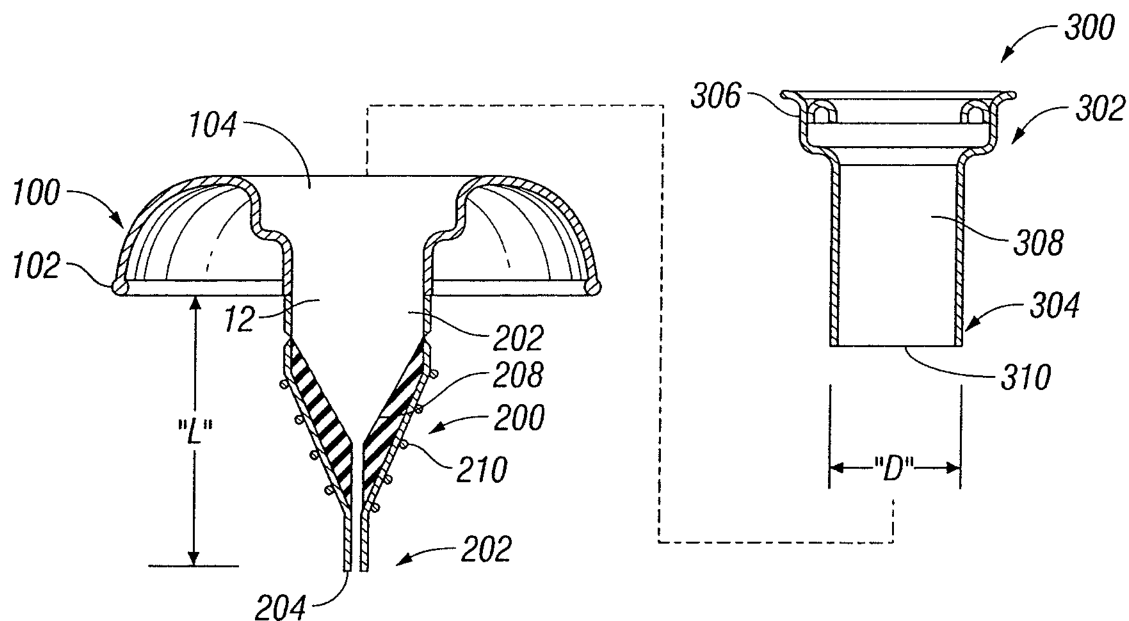
FIG. 2 is a side cross-sectional view of the surgical anchoring apparatus of FIG. 1 with the dilator element removed from the body member.
Figure 3:
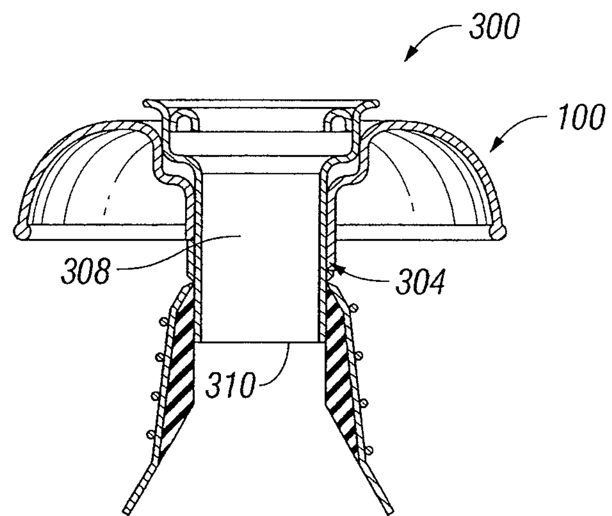
FIG. 3 is a side cross-sectional view of the surgical anchoring apparatus of FIG. 2 with the dilator element inserted in the body member.

With reference now to FIGS. 1-2, a surgical anchoring apparatus 1000 is disclosed for use in a surgical procedure, e.g. a minimally invasive procedure. Anchoring apparatus 1000 includes a body member 10 and a dilator element 300 at least partially positionable therein. Body member 10 defines a longitudinal axis “A” and a longitudinally extending passage 12 and includes a grip segment 100 and an expandable section 200.

Figure 6:
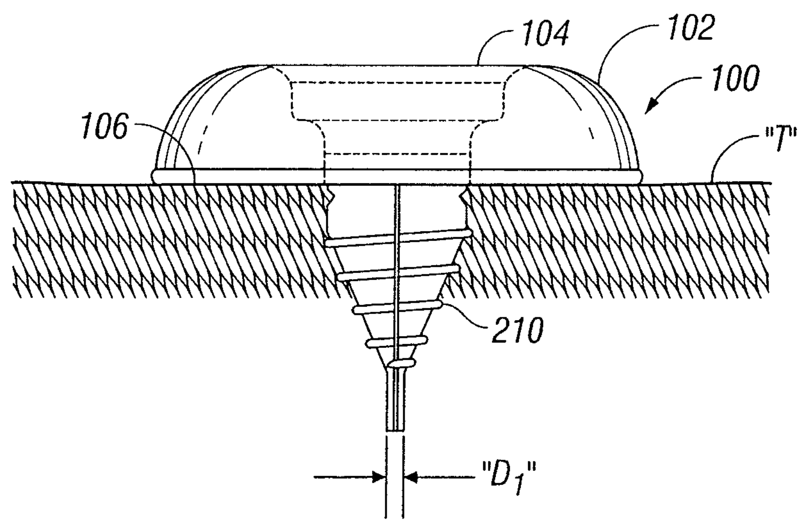
FIG. 6 is a side plan view of the body member of the surgical anchoring apparatus illustrating the grip segment in a second normal state.

Grip segment 100 depends radially outward relative to the longitudinal axis “A” of body member 10 and includes an outer surface 102 having an aperture 104 formed therein that is dimensioned to receive dilator element 300. Outer surface 102 extends outwardly from aperture 104 to a peripheral flange 106. Peripheral flange 106 is adapted to contact and establish a substantially vacuum quality seal with tissue “T” (see FIGS. 6-7), as discussed below.

Figure 4:
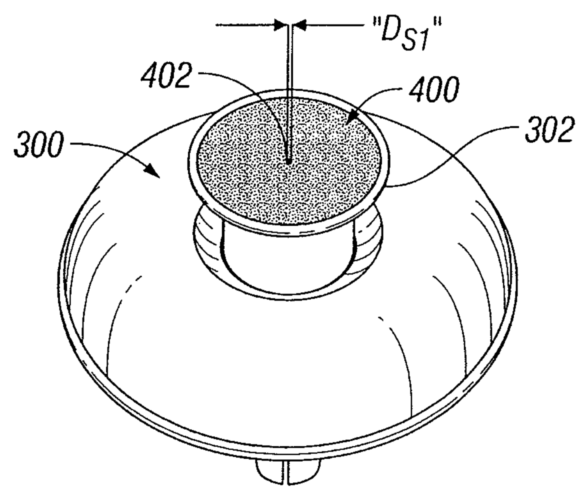
FIG. 4 is a top perspective view of the surgical anchoring apparatus of FIG. 1 illustrating details of the seal.
Figure 5:
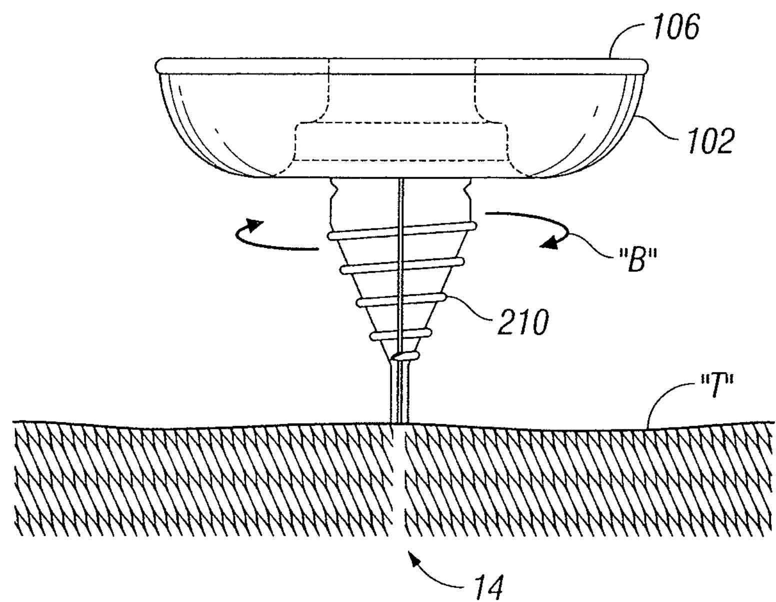
FIG. 5 is a side plan view of the body member of the surgical anchoring apparatus illustrating the grip segment in a first inverted state.

Grip segment 100 is adapted for manual engagement by a user and to resiliently transition between a first or normal state (FIGS. 1-4) and a second state (FIG. 5). In the first state, outer surface 102 of grip segment 100 exhibits a substantially distal curvature in which peripheral flange 106 is directed distally. In the second state, grip segment 100 is at least partially inverted such that at least a portion of outer surface 102 exhibits a substantially proximal curvature such that peripheral flange 106 is directed proximally. In this state, grip segment 100 is more aptly configured for manual engagement by a user to facilitate the insertion of expandable section 200 into an incision 14 (FIG. 5), as discussed in further detail below. It should be noted that engagement by a user is also possible when grip segment 100 is in the first state. Grip segment 100 may be formed of any suitable biocompatible material that is sufficiently flexible to permit grip segment 100 to resiliently transition between the first and second states, including but not being limited to elastomeric materials.

Figure 7:
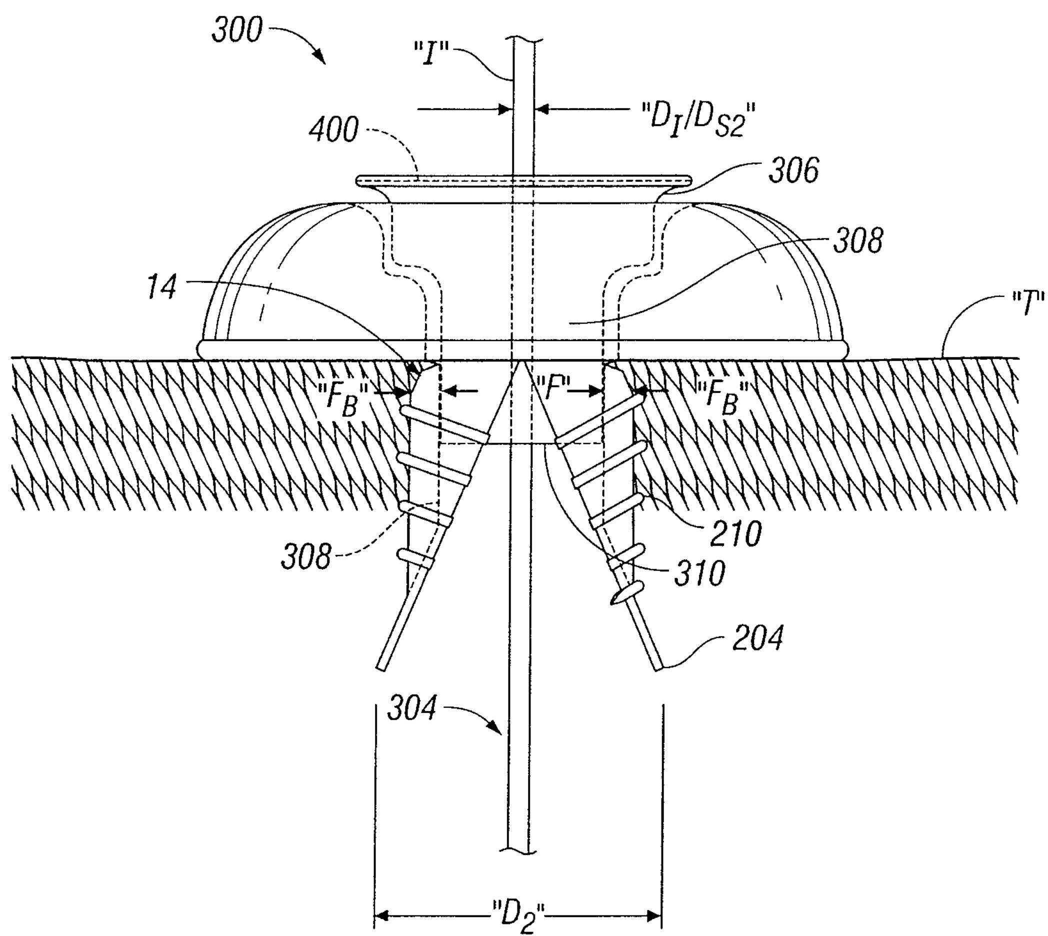
FIG. 7 is a side plan view of the surgical anchoring apparatus illustrating the dilator element inserted through the body member, and an expandable section of the body member in a second, expanded condition.

Expandable section 200 extends distally from grip segment 100 and is in substantial alignment with aperture 104 of grip segment 100 such that dilator element 300 may pass through aperture 104 and into expandable section 200 upon insertion. At its distal end 202, expandable section 200 defines an opening 204 that is dimensioned to allow a distal end 304 of dilator element 300 to pass therethrough. Expandable section 200 is adapted to transition from a first, or initial condition (FIG. 6) to a second, or expanded condition (FIG. 7).

Expandable section 200 defines a length “L” that is sufficient to provide percutaneous access to a patient’s underlying cavities, organs and the like (not shown). Expandable section 200 includes a plurality of expandable segments 206, a plurality of internal cam surfaces 208 and an outer helical thread 210.

Expandable segments 206 are defined by two or more slots 212. In one embodiment, slots 212 extend in a substantially longitudinal manner. However, alternate configurations for slots 212 are not beyond the scope of the present disclosure. Upon the transition of expandable section 200 from the initial condition to the expanded condition, expandable segments 206 are splayed radially outward, as discussed in further detail below.

Internal cam surfaces 208 are obliquely arranged with respect to the longitudinal axis “A” defined by body member 10. Internal cam surfaces 208 are configured to engage a tapered outer surface 308 of dilator element 300 upon its insertion into longitudinal passage 12 of body member 10 to facilitate the transition of expandable section 200 from the initial condition to the expanded condition, as discussed in further detail below. In one embodiment, each expandable segment 206 includes an internal cam surface 208. Outer helical thread 210 is disposed on the outer surface of expandable section 200. Helical thread engages tissue “T” upon the insertion of expandable section 200 into incision 14 so as to facilitate the distal advancement of body member 10. In addition, helical thread 210 may assist in the anchoring of body member 10 within tissue “T”.

Expandable section 200 may be formed of any suitable biocompatible material that is sufficiently resilient to permit resilient expandable section 200 to resiliently transition between the initial and expanded conditions thereof.

In its first, or normal condition, expandable section 200 is configured for insertion into incision 14 and defines a first diameter “$D_1$”. Upon the insertion of dilator element 300, a distal end 304 thereof engages cam surfaces 208. As dilator element 300 is advanced distally through longitudinal passage 12, its distal end 304 forces cam surfaces 208, and expandable segments 206, outwardly to thereby transition expandable section 200 into its expanded condition. In its expanded condition, expandable section 200 defines a second, larger diameter “$D_2$”.

Dilator element 300 has a proximal end 302 that includes a seal 400 and a gripping portion 306 that is configured for grasping by a user during the distal advancement of dilator element 300 through body member 10.

Dilator element 300 defines a longitudinal passage 308 that extends therethrough from its proximal end 302 to its distal end 304 where an opening 310 is defined. Longitudinal passage 308 defines a diameter “D” and is configured to removably receive one or more surgical objects “I” (FIG. 7), e.g. a trocar, endoscope or surgical stapler. The diameter “D” of longitudinal passage 308 may range between about 3 mm to about 15 mm, or may be substantially within the range of about 5 mm to about 12 mm. However, the use of surgical objects having substantially larger and smaller diameters is contemplated herein, as is a dilator element 300 defining a longitudinal passage 308 with a substantially larger or smaller diameter “D” so as to accommodate such surgical objects. In one embodiment, the longitudinal dilator passage 308 is divided into a plurality of individual lumens (not shown) separated by at least one septum. Each of the individual lumens may be of either substantially similar or substantially different dimensions and are each configured to receive a surgical object.

Dilator element 300 may be formed of any biocompatible material that is sufficiently rigid to urge the expandable segments 206 of expandable section 200 outwardly upon its insertion into longitudinal body passage 12 and thereby transition expandable portion 200 from its normal condition to its expanded condition.

Referring now to FIGS. 4 and 7, seal 400 is associated with proximal end 302 of dilator element 300 and may be mounted thereto. Seal 400 defines an aperture 402 and is adapted to transition from a closed condition (FIG. 4) to an open condition (FIG. 7) upon the insertion of surgical object “I”. In the closed condition, aperture 402 defines a first dimension “$D_{S1}$” of about 0 mm so as to substantially prevent the escape of any insufflation gas (not shown) therethrough in the absence of surgical object “I”. Upon the insertion of surgical object “I”, aperture 402 is forced open, thereby transitioning seal 400 into the open condition. In this condition, aperture 402 defines a second dimension “$D_{S2}$” that substantially approximates the diameter “$D_I$” of surgical object “I” such that seal 400 forms a substantially fluid-tight seal with surgical object "I", thereby substantially preventing the escape of any insufflation gas through seal 400. Surgical object "I" will generally define a diameter substantially within the range of about 5 mm to about 12 mm. Accordingly, in the second condition, aperture 402 will generally define a second dimension "$D_{S2}$" that is also substantially within the range of about 5 mm to about 12 mm. However, the use of surgical objects having substantially larger and smaller diameters is contemplated herein, as is a seal 400 with an aperture 402 that is capable of accommodating such surgical objects.

Seal 400 may be formed of any suitable biocompatible material that is at least semi-resilient in nature such that seal 400 may transition between the closed and open conditions thereof. Seal 400 may be any seal or valve suitable for the intended purpose of removably receiving a surgical object in sealed relation therewith, including but not being limited to a slit-valve or a zero closure valve.

The use and function of anchoring apparatus 1000 during the course of a minimally invasive procedure will now be discussed. Initially, the peritoneal cavity (not shown) is insufflated with a suitable biocompatible gas such as, e.g., $CO_2$ gas, such that the cavity wall is raised and lifted away from the internal organs and tissue housed therein, providing greater access thereto. The insufflation may be performed with an insufflation needle or similar device, as is conventional in the art. Either prior or subsequent to insufflation, an incision 14 is created in tissue "T", the dimensions of which may be varied dependent upon the nature of the surgical procedure.

Prior to the insertion of anchoring apparatus 1000 within incision 14, dilator element 300 is removed from body 10. Thereafter, the clinician may transition grip segment 100 from the first state (FIGS. 1-4) to the second state (FIG. 5) to facilitate the manual engagement thereof and the insertion of body member 10. To realize this transition, the user at least partially inverts grip segment 100 such that the outer surface 102 exhibits a proximal curvature. Once in the second state, the clinician may more easily grasp grip segment 100, e.g. about peripheral flange 106.

The distal end 206 of expandable section 200 is then inserted into and advanced distally through incision 14. Optionally, the clinician may rotate body 10, e.g. clockwise in the direction of arrows "B", during insertion such that helical thread 210 facilitates the distal advancement of expandable section 200. After expandable section 200 has been completely inserted within the patient's tissue "T", grip segment 100 is returned to its first state such that peripheral flange 106 is in engagement with tissue "T". Grip segment 100 may form a substantially vacuum seal with tissue "T". (See FIGS. 6-7).

Subsequently, dilator element 300 is inserted through aperture 104 in grip segment 100, into longitudinal body passage 202, distally therethrough and into expandable section 200. During the distal advancement of dilator element 300, its distal end 304 engages cam surfaces 208, thereby forcing the plurality of expandable segments 206 outwardly and transitioning expandable section 200 from the normal condition (FIG. 6) to the expanded condition (FIG. 7). As previously discussed, in the normal condition, expandable section 200 defines a first diameter "$D_1$" and in the expanded condition, expandable section 200 defines a second, larger diameter "$D_2$".

During the transition from the first condition to the second condition, expandable section 200 expands outwardly and exerts a force "F" upon tissue "T" which dilates incision 14. Force "F" creates a corresponding biasing force "$F_B$" within tissue "T" that attempts to close incision 14. Forces "F" and "$F_B$" collaborate to secure and anchor expandable section 200 within tissue "T" in a substantially fluid tight manner such that the escape of insufflation gas about anchoring apparatus 1000 is substantially prevented. In addition, while inserted within tissue "T", helical thread 210 is disposed distally, and perhaps proximally, of tissue "T", thereby further securing the disposition and anchoring of expandable section 200 within tissue "T".

Finally, surgical object "I" is inserted and advanced distally through the seal 400 associated with the proximal end 302 of dilator element 300, through longitudinal dilator passage 308 and ultimately through opening 310 at the distal end 304 of dilator element 300. Thereafter, the remainder of the surgical procedure may be carried out using surgical object "I".

Upon completion of the surgical procedure, surgical object "I" is withdrawn from dilator element 300 through seal 400. Dilator element 300 is then withdrawn from expandable section 200 through longitudinal body passage 202 and through aperture 104 in grip segment 100. During the withdrawal of dilator element 300, force "F" dissipates, as does the corresponding biasing force "$F_B$" in tissue "T", thereby facilitating the withdrawal of expandable section 200. The user may then transition grip segment 100 from the first state to the second state and withdraw body member 10 from incision 14, optionally rotating body member 10 during withdrawal. Incision 14 may then be closed.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical anchoring apparatus configured and dimensioned for positioning within tissue, which comprises:

a body member having proximal and distal ends, and defining a longitudinal body passage extending along a longitudinal axis of the body member, the body member including an expandable section adapted to transition between a first initial condition and a second expanded condition, wherein the body member includes a grip segment adapted for manual engagement by a user depending radially outwardly relative to the longitudinal axis of the body member, the grip segment being adapted to transition between a normal state and an at least partially inverted state, the grip segment being secured to the proximal end of the body member such that the grip segment extends proximally from the body member;

a dilator element at least partially positionable within the longitudinal passage of the body member, and being dimensioned to cause the expandable section to transition to the second expanded condition during insertion of the dilator element in the longitudinal passage, to thereby facilitate securement of the body member relative to tissue, the dilator element defining a longitudinal dilator passage for reception and passage of a surgical object; and a seal secured to the dilator element, the seal adapted to establish a substantial sealing relation with the surgical object received within the dilator element.

2. The surgical anchoring apparatus according to claim 1 wherein the expandable section of the body member includes a plurality of expandable segments.

3. The surgical anchoring apparatus according to claim 2 wherein the expandable section includes a plurality of internal cam surfaces extending inwardly from an internal surface of the expandable section and obliquely arranged with respect to the longitudinal axis, the dilator element being dimensioned to contact the cam surfaces during insertion of the dilator element within the longitudinal passage of the body member to move the expandable segments at least radially outwardly relative to the longitudinal axis and cause the transition of the expandable section to the second expanded condition.

4. The surgical anchoring apparatus according to claim 3 wherein each expandable segment includes an internal cam surface.

5. The surgical anchoring apparatus according to claim 4 wherein adjacent expandable segments of the expandable section of the body member are separated by slots.

6. The surgical anchoring apparatus according to claim 5 wherein adjacent expandable segments are separated by substantially longitudinal slots.

7. The surgical anchoring apparatus according to claim 3 wherein the expandable section includes an outer helical thread adapted to facilitate advancement of the body member within the tissue when the body member is in the first initial condition.

8. The surgical anchoring apparatus according to claim 1 wherein the grip segment comprises an elastomeric material.

9. The surgical anchoring apparatus according to claim 8 wherein the grip segment includes a peripheral flange oriented towards the tissue in the normal state such that the peripheral flange is positioned to contact the tissue, and oriented away from the tissue in the at least partially inverted state.

10. The surgical anchoring apparatus according to claim 9 wherein the peripheral flange is adapted to establish a vacuum seal with the tissue during transition of the grip segment from the at least partially inverted state to the normal state.

11. The surgical anchoring apparatus according to claim 1 wherein the seal includes a gel material.

12. The surgical anchoring apparatus according to claim 1 wherein the seal includes a self healing foam material.

13. The surgical anchoring apparatus according to claim 1 wherein the expandable section includes a first portion defining a transverse cross-sectional dimension that decreases in a proximal direction, whereby the first portion of the expandable section is tapered in configuration, and a second portion positioned adjacent a distal end of the first portion, the second portion having a substantially constant transverse cross-sectional dimension.

14. A surgical anchoring apparatus configured and dimensioned for positioning within tissue, which comprises:

a grip segment configured and dimensioned for engagement with an outer surface of the tissue, the grip segment being adapted to transition between a normal state, wherein a peripheral portion of the grip segment is oriented towards the tissue, and an at least partially inverted state, wherein the peripheral portion of the grip segment is oriented away from the tissue;

an expandable section having a proximal end secured to the grip segment such that the expandable section extends distally from the grip segment, and a distal end opposite the proximal end, the expandable section defining a longitudinal axis, and being configured and dimensioned for movement between an initial condition and an expanded condition; and a dilator element configured and dimensioned for insertion into the expandable section to cause the expandable section to transition to the second expanded condition during advancement of the dilator element through the expandable section to thereby facilitate securement of the expandable section relative to the tissue.

15. The surgical anchoring apparatus according to claim 14 wherein the dilator element defines a longitudinal passage configured and dimensioned to receive a surgical object.

16. The surgical anchoring apparatus according to claim 15 further including a seal secured to the dilator element, the seal being configured and dimensioned to receive the surgical object in substantially sealed relation upon insertion of the surgical object into the longitudinal passage of the dilator element.

17. The surgical anchoring apparatus according to claim 14 wherein the expandable section includes a plurality of expandable segments.

18. The surgical anchoring apparatus according to claim 17 wherein the expandable section includes a plurality of internal cam surfaces extending inwardly from an internal surface of the expandable section, the internal cam surfaces being obliquely arranged with respect to the longitudinal axis, the dilator element being configured and dimensioned to contact the cam surfaces to move the expandable segments radially outwardly relative to the longitudinal axis, and thereby move the expandable section into the expanded condition.

19. The surgical anchoring apparatus according to claim 18 wherein each expandable segment includes an internal cam surface.

20. The surgical anchoring apparatus according to claim 17 wherein adjacent expandable segments of the expandable section are separated by slots.

21. The surgical anchoring apparatus according to claim 20 wherein the slots are substantially linear in configuration.

22. The surgical anchoring apparatus according to claim 14 wherein the expandable section includes an outer helical thread configured and dimensioned to facilitate advancement of the expandable section through the tissue when the expandable section is in the initial condition.

23. The surgical anchoring apparatus according to claim 14 wherein the grip segment is configured and dimensioned for manual engagement by a user.

24. The surgical anchoring apparatus according to claim 14 wherein the grip segment depends radially outwardly relative to the longitudinal axis.

25. The surgical anchoring apparatus according to claim 14 wherein the grip segment comprises an elastomeric material.

26. The surgical anchoring apparatus according to claim 14 wherein the grip segment includes a peripheral flange configured and dimensioned to contact the tissue when the grip segment is in the normal state.

27. The surgical anchoring apparatus according to claim 26 wherein the peripheral flange is configured and dimensioned to form a vacuum seal with the tissue as the grip segment transitions from the at least partially inverted state to the normal state.

28. The surgical anchoring apparatus according to claim 9 wherein the grip segment is positioned in a convex orientation in the normal state, wherein an outer surface of the grip segment extends towards the tissue such that the grip segment defines a cross-sectional dimension increasing in a distal direction, and the grip segment is positioned in a concave orientation in the at least partially inverted state, wherein an outer surface of the grip segment extends away from the tissue such that the grip segment defines a cross-sectional dimension decreasing in a distal direction.

29. The surgical anchoring apparatus of claim 14 wherein the grip segment is positioned in a convex orientation in the normal state, wherein an outer surface of the grip segment extends towards the tissue such that the grip segment defines a cross-sectional dimension increasing in a distal direction, and the grip segment is positioned in a concave orientation in the at least partially inverted state, wherein an outer surface of the grip segment extends away from the tissue such that the grip segment defines a cross-sectional dimension decreasing in a distal direction.

* * * * *